(12) United States Patent
Tseng et al.

(10) Patent No.: US 8,229,544 B2
(45) Date of Patent: Jul. 24, 2012

(54) DETECTING TEMPERATURE AND PROTEIN DENATURATION DURING THERMAL THERAPY

(75) Inventors: Wen-Yih Isaac Tseng, Taipei (TW); Hsu-Hsia Peng, Taipei (TW); Teng-Yi Huang, Taipei (TW); Hsiao-Wen Chung, Taipei (TW)

(73) Assignee: National Health Research Institutes, Miaoli County (TW)

(*) Notice: Subject to any disclaimer, the term of this patent is extended or adjusted under 35 U.S.C. 154(b) by 1028 days.

(21) Appl. No.: 12/115,143

(22) Filed: May 5, 2008

(65) Prior Publication Data
US 2008/0275331 A1 Nov. 6, 2008

(51) Int. Cl.
*A61B 5/05* (2006.01)
*G01V 3/00* (2006.01)
(52) U.S. Cl. .................. 600/412; 600/411; 324/315
(58) Field of Classification Search .............. 601/2, 3; 600/412, 411, 410; 382/128
See application file for complete search history.

(56) References Cited

U.S. PATENT DOCUMENTS
6,735,461 B2  5/2004  Vitek et al.
7,771,418 B2 * 8/2010  Chopra et al. ............. 606/28

FOREIGN PATENT DOCUMENTS
WO  WO 2006/027783  3/2006

OTHER PUBLICATIONS

Ong et al., "Sliding window dual-gradient echo (SW-dGRE): T1 and proton resonance frequency (PRF) calibration for temperature imaging in polyacrylamide gel", Physics in Medicine and Biology, pp. 1917-1931, 2003.*

Peng, et al., "Simultaneous Monitoring of Temperature and Magnetization Transfer for HIFU Treatment", Proc. Intl. Soc. Mag. Reson. Med. (14th ISMRM), Seattle, May 6-12, 2006.*
Graham et al., "Analysis of Changes in MR Properties of Tissues after Heat Treatment", Magnetic Resonance in Medicine, 42:1061-1071, 1999).*
Ishihara et al., "A precise and Fast Temperature Mapping Using Water Protein Chemical Shift," Magnetic Resonance in Medicine, vol. 34, Issue 6, pp. 814-823.
Haase et al., "Flash Imaging, Rapid NMR Imaging Using Low Flip-Angle Pulses," Journal of Magnetic Resonance, 67:258-266 (0986).
Yu et al., "Differentiating Between T1 and T2 Chnages Caused by Gadopentetate Dimeglumine in the Kidnet by Using a Double-Echo Dynamic MR Imaging Sequence," JMRI, 6:764-768 (1996). A. Haase, "Snapshot FLASH MRI. Applications to T1, T2, and Chemical-Shift Imaging," Magnetic Resonance in Medicine, 13:77-89 (1990).
Henkelman et al., "Magnetization Transfer in MRI; A Review," NMR in Biomed., 14:57-64 (2001).
Yeo et al., "Zero and First-Order Phase Shift Correction for Filed Map Estimation with Dual-Echo GRE Using Bipolar Gradients," Magnetic Resonance Imaging, 25:1263-1271 (2007).
Williams, Catherine F. M. and Thomas W. Redpath, "Source of Artifact and Systematic Error in Quantitative Snapshot Flash Imaging and Methods for their Elimination," Magnetic Resonance in Medicine, 41:63-71 (1999).

* cited by examiner

*Primary Examiner* — Long V. Le
*Assistant Examiner* — Katherine Fernandez
(74) *Attorney, Agent, or Firm* — Occhiuti Rohlicek & Tsao LLP

(57) ABSTRACT

In one aspect, in general, a method is provided for detecting temperature and protein denaturation of a tissue during thermal therapy. The method includes generating a plurality of MR pulse sequences that include a first group of pulse sequences and a second group of pulse sequences, and receiving a plurality of response signals that include a first and second group of response signals in response to the first and second groups of pulse sequences, respectively. A first information associated with a degree of protein denaturation of the tissue is determined based on the first and second groups of response signals. A second information associated with a temperature of the tissue is determined based on at least some of the plurality of response signals.

26 Claims, 10 Drawing Sheets

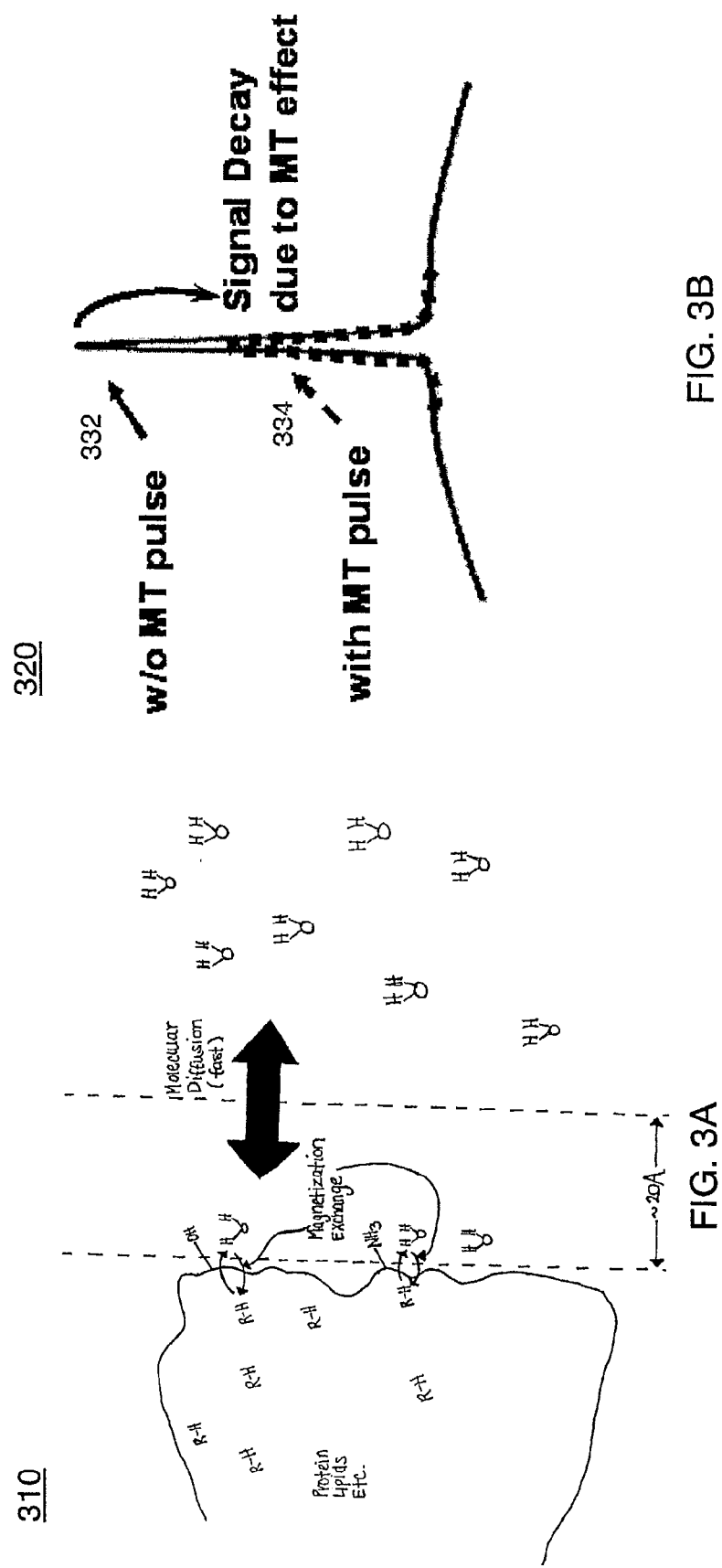

DETECTING TEMPERATURE AND PROTEIN DENATURATION DURING THERMAL THERAPY

CROSS-REFERENCE TO RELATED APPLICATIONS

This application claims the benefit of U.S. Provisional Application No. 60/915,846, filed May 3, 2007, and U.S. Provisional Application No. 60/924,250, filed May 4, 2007, the contents of which are incorporated herein by reference.

BACKGROUND

This application generally relates to detecting temperature and protein denaturation during thermal therapy.

Recent development in thermal ablation techniques holds great promise for cancer treatment. High intensity focused ultrasound (HIFU), for example, uses focused ultrasound to induce a localized temperature elevation, causing irreversible tissue necrosis in a target tumor. The amount of energy (i.e., thermal dose) is preferably controlled so that such procedures can be both safe and effective. One approach to determining thermal dose uses magnetic resonance imaging (MRI) techniques to measure changes in tissue temperature, which provides an indirect estimate on the degree of tissue necrosis. However, during these MRI-guided thermal procedures, errors may be introduced into temperature measurements by many factors, such as movements of the object being imaged and dynamic changes in magnetic field intensity. Therefore, MRI-based temperature measurements alone may not provide sufficient guidance for administering thermal procedures.

SUMMARY

In one aspect, in general, a method is provided for detecting temperature and protein denaturation of a tissue during thermal therapy. The method includes generating a plurality of MR pulse sequences that include a first group of pulse sequences and a second group of pulse sequences, and receiving a plurality of response signals that include first and second groups of response signals in response to the first and second groups of pulse sequences, respectively. A first information associated with a degree of protein denaturation of the tissue is determined based on the first and second groups of response signals. A second information associated with a temperature of the tissue is determined based on at least some of the plurality of response signals.

Aspects can include one or more of the following features.

The plurality of MR pulse sequences are configured to be suitable for inducing response signals that are sufficient for determining the first and second information. Suitable MR pulse sequences may include, for example, "dual gradient echo sequences."

Each one of the first group of pulse sequences may include a RF excitation pulse, and each one of the second group of pulse sequences may include the RF excitation pulse and an MT pulse. The MT pulse may include an off-resonance pulse. The MT pulse is configured to cause a change in the response signals induced by the RF excitation pulse alone.

The first and second groups of pulse sequences may be interleaved.

Each one of the plurality of response signals may include a first echo component and a second echo component. The first information may be determined from comparing the first group of response signals with the second group of response signals. The first information may be further determined from comparing at least some of the first echo components of the first group of response signals with some of the first echo components of the second group of response signals.

The first information includes a magnetization transfer ratio, and the second information includes a phase information.

The method may further include reconstructing an image and forming a temperature map of the tissue based on the plurality of response signals.

In another aspect, in general, a method is provided for MRI-guided thermal therapy on a tissue. The method includes generating a plurality of MR pulse sequences and receiving a response signal for each of the plurality of MR pulse sequences. A first information associated with a degree of protein denaturation of the tissue and a second information associated with a temperature of the tissue are determined based on the response signals. Specifications of a treatment plan are accepted. The treatment plan includes a plurality of sessions, each being associated with one of a plurality of regions of the tissue and controlled based on the first and second information.

Aspects may include one or more of the following features.

The method may further include initiating and terminating each of the plurality of sessions based on the first and second information. The treatment plan may include a criterion for initiating and terminating each of the plurality of sessions. The criterion may be associated with the temperature of the tissue, and/or with the level of protein denaturation of the tissue.

In another aspect, in general, a system is provided for detecting temperature and protein denaturation on a tissue. The system includes a controller that generates a plurality of pulse sequences, including a first group of pulse sequences and a second group of pulse sequences, and receives a plurality of response signals. The plurality of response signals include a first group of response signals in response to the first group of pulse sequences, and a second group of response signals in response to the second group of pulse sequences. The controller determines a first information associated with a degree of protein denaturation of the tissue and a second information associated with a temperature of the tissue based on the plurality of response signals.

Aspects may include one or more of the following features.

The system may further include a subsystem for delivering the plurality of pulse sequences and detecting the plurality of response signals. The subsystem may include a MRI system, and the plurality of pulse sequences may include MR pulse sequences.

The plurality of pulse sequences are configured to be suitable for inducing response signals that are sufficient for determining the first and second information. Suitable pulse sequences include, for example, "dual gradient echo sequences."

Each one of the first group of pulse sequences may include a RF excitation pulse, and each one of the second group of pulse sequences may include the RF excitation pulse and a MT pulse.

Each one of the plurality of response signals may include a first echo component and a second echo component, and the controller determines the first information based on at least some of the first echo components of the first group of response signals and at least some of the first echo components of the second group of response signals.

The controller may be further configured for reconstructing an image and forming a temperature map of the tissue based on the plurality of response signals.

Among other features and advantages, aspects of the invention provide a system that uses novel magnetic resonance imaging pulse sequences for detecting and monitoring in real-time both the temperature and protein denaturation in tissues. By exciting target tissues, such pulse sequences (e.g., dual gradient echo sequences that are interleaved with MT pulses) induce response signals that are sufficient for determining the temperature and the level of protein composition. Important feedback, which is useful in many clinical applications including thermal therapy (such as HIFU treatment), is provided to medical professionals. For example, compared with conventional HIFU procedures, MRI-guided HIFU procedures can increase the accuracy of thermal ablation and minimize damage to adjacent normal tissues. In addition, systems using such approaches can be used to evaluate protein denaturation of HIFU-induced lesions during or after HIFU heating procedures. Other features and advantages are apparent from the following description, and from the claims.

DESCRIPTION OF DRAWINGS

FIGS. 3A-3C are diagrams illustrating the use of magnetization transfer ratio technique.

DETAILED DESCRIPTION

1 Thermal Ablation

Thermal ablation makes use of heating techniques that use radio frequency (RF) energy, microwave energy, acoustic energy (e.g., focused ultrasound), or optical energy (e.g., laser light) to induce localized temperature elevation for damaging target tissues. Focused ultrasound, for instance, can be used to provide a non-invasive ablation means on human tumor tissues, e.g., by vibrating tumor cells and generating heat that destroys the cells.

In some examples, high intensity focused ultrasound (HIFU) is delivered via a concave transducer that focuses ultrasound beam into areas of interest. One example of such a HIFU system provides a focus distance at a depth of 10 cm, and a focal lesion with length of 10 mm and a cross sectional diameter of 2 mm. This small cross-sectional dimension of focal lesion allows HIFU to be focused on target tumor without injuring surrounding tissues. HIFU techniques have been developed and are now in clinical trials in many countries. With the potential to overcome limitations of thermal therapy that uses other energy sources, HIFU technique is a useful non-invasive surgical technique for cancer treatment.

2 MRI-Guided HIFU

Magnetic resonance imaging (MRI) techniques are widely used in medical imaging to provide anatomic, pathological and physiological information of living tissues. In general, MRI uses a strong static magnetic field to align the magnetization of hydrogen nucleus (protons) in the body. RF excitation pulses at resonance frequency are then applied to alter the alignment of this magnetization, causing the magnetization of the protons to precess about the magnetic field producing a rotating magnetic field detectable by a receive coil of a MRI scanner. In the presence of properly time-sequenced magnetic field gradient, magnetic resonance signals generated by the RF excitation pulses can be used to reconstruct cross-sectional images of the body. As a non-invasive imaging technique, MRI can be used to guide the HIFU techniques (or possibly other thermal therapy techniques) to provide safe and accurate thermal treatment procedures for patients.

Figure 1:
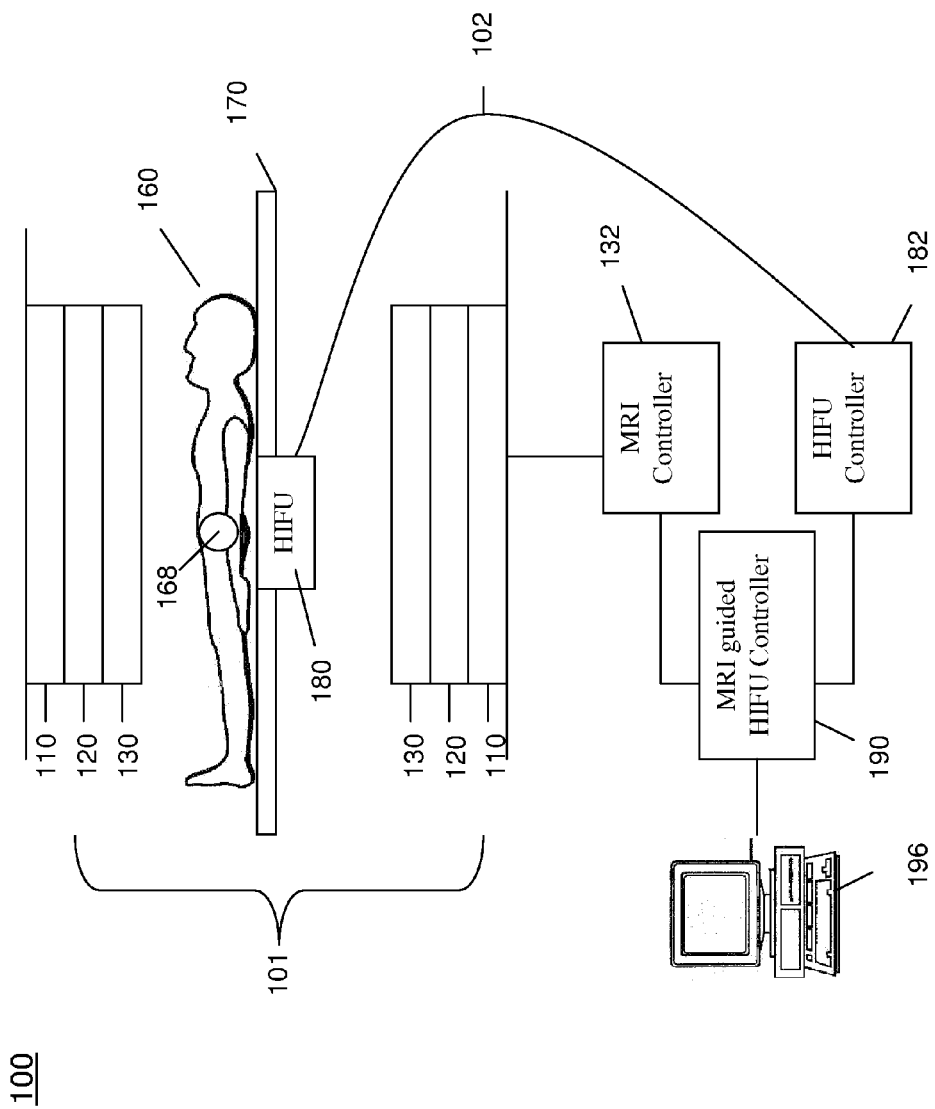
FIG. 1 is a schematic diagram of an exemplary MRI-guided HIFU system.

FIG. 1 shows an example of a MRI-guided HIFU system 100, including a MRI subsystem 101 and a HIFU subsystem 102. The MRI subsystem 101 includes a magnet 110 for generating a static magnetic field, gradient coils 120 for generating spatially distributed magnetic field gradients in three orthogonal coordinates, and RF coils 130 for exciting and receiving RF signals. Signals received by the RF coils 130 are transmitted to a MRI controller 132 and are further reconstructed into images displayed in a display console 196. The HIFU subsystem 102 includes a HIFU transducer 180 and a HIFU controller 182. Both the MRI Controller 132 and the HIFU controller 182 communicate bi-directionally with a MRI guided HIFU Controller 190.

During a MRI-guided HIFU procedure, a patient 160 lies on a table 170. The HIFU transducer 180 is movable (not shown in the figure) and controlled by the instructions of the HIFU controller 182, based on MR imaging information obtained on the MRI guided HIFU Controller 190, to transmit focused ultrasound pulses into target tissue 168 of the patient 160. The display console 196 is used by the medical professionals to perform adjustment of the system, to plan the treatment procedures, and to monitor the operation in real-time.

Figure 2:
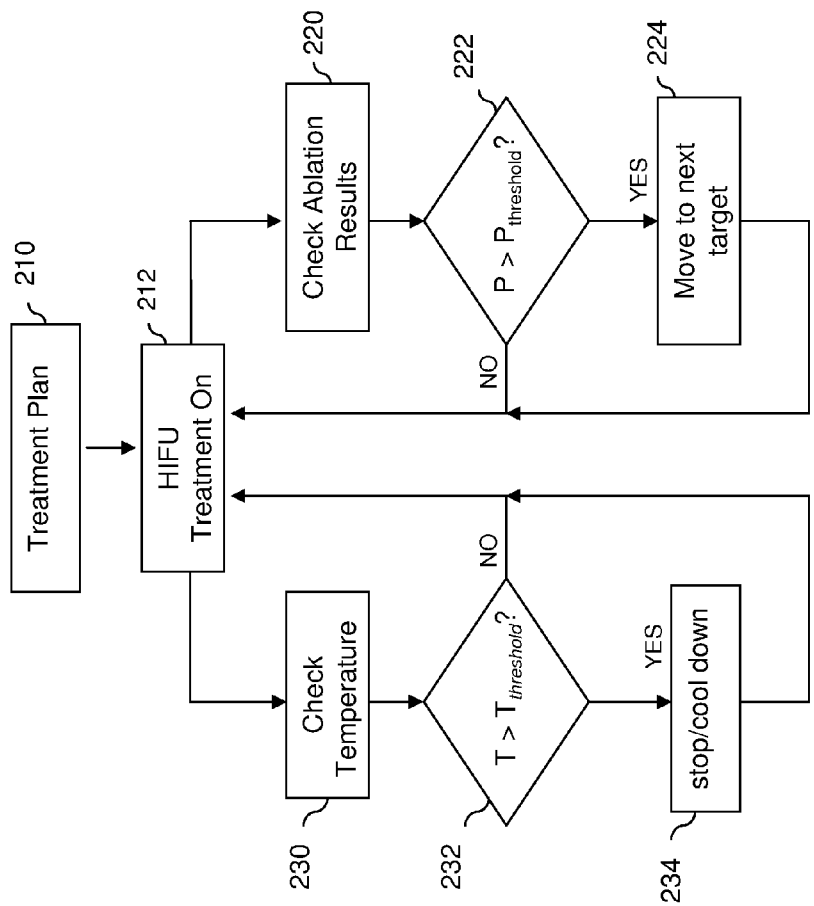
FIG. 2 is a flow chart illustrating a procedure of monitoring temperature and protein denaturation in real-time during thermal therapy.

Referring to FIG. 2, the MRI-guided HIFU system 100 integrates the use of MRI and HIFU subsystems into one procedure 200. Initially, in a step 210, medical professionals determine a treatment plan for the patient 160, e.g., by taking pre-treatment medical measurements (such as magnetic resonance images) to obtain anatomical and physiological information related to this patient. The treatment plan may include a number of treatment sessions each associated with a specific target region, and criteria for initiating and terminating these sessions. The criteria may be related to the temperature of the tissue, and/or the level of protein composition.

In one implementation of such a treatment plan, in a step 212, a HIFU treatment session is initiated. During this session, the system 100 monitors in real-time both a temperature of the target tissue T (in step 230) and the result of thermal ablation based on a measured degree of protein denaturation P (in step 220). If, in step 232, the measured temperature T has exceeded a predetermined threshold $T_{threshold}$, the system 100 stops the exposure of HIFU energy to the tissue or enters a cool down period (step 234). If, in step 222, the measured degree of protein denaturation P has exceeded a predetermined threshold $P_{threshold}$, indicating that desired ablation results have been achieved, the current treatment session is terminated. A subsequent session is initiated, after the HIFU transducer 180 has been moved to an adjacent pre-planned location to treat another target (step 224).

During this HIFU procedure 200, the temperature T and the degree of protein denaturation P in the same region are measured by the MRI subsystem 101 using a proton resonance frequency shift technique and a magnetization transfer ratio technique, respectively. These two techniques are described in greater detail in the following sections.

3 Magnetization Transfer Ratio

The magnetization transfer ratio (MTR) technique measures the level of protein composition in tissues by observing a change in detectable MR signals caused by magnetization transfer (MT) pulses. Generally, MT pulses are excitation signals that cause off-resonance magnetization saturation. For example, MT pulses are off-resonance RF (radio frequency) pulses applied in conjunction with RF excitation pulses (e.g., on-resonance RF pulses). Conventional MRI systems use RF excitation pulses to induce response signals (e.g., detectable proton signals from free water molecules). The application of a MT pulse saturates proton magnetization in macromolecules. As these protons with saturated magnetization enter the pool of free protons (primarily in water molecules), or transfer their magnetization with that of free water protons, the intensity of detectable response signal which comes primarily from free water molecules is decreased. This change in the intensity indicates a level of magnetization transfer effect in the tissue, and is used for analyzing the level of protein composition in tissues.

Figure 3C:
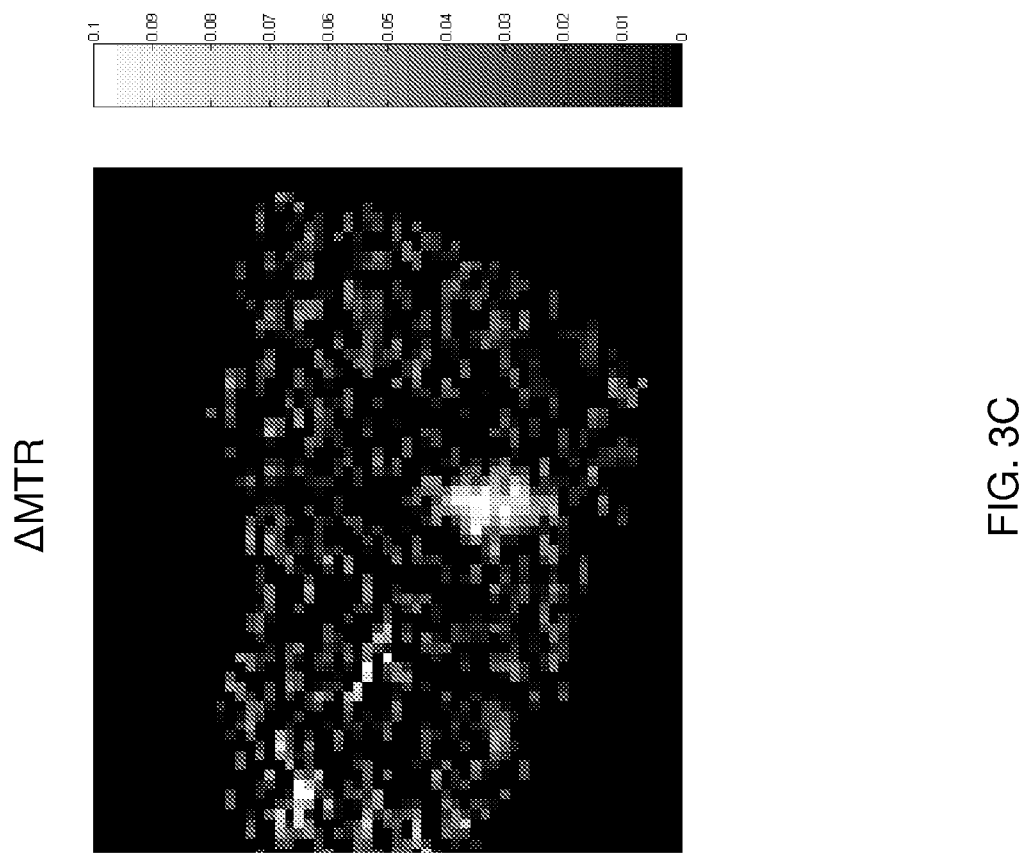

FIGS. 3A to 3C illustrate the use of MTR technique in greater detail. Diagram 310 depicts the phenomenon of magnetization exchange between water and macromolecules, which is also described by Henkelman et. al., in *Magnetization Transfer in MRI: A Review*, NMR Biomed. 2001 April; 14(2):57-64, the disclosure of which is incorporated herein by reference. If a tissue is exposed to a RF excitation pulse, a water signal 332 is detected. If, the same tissue is exposed to a MT pulse before the RF pulse, the MT pulse causes magnetization saturation of macromolecule protons, resulting in a new water signal 334 at a lower intensity through the magnetization transfer process. The normalized difference in magnitude between these two water signals 332 and 334 is proportional to the magnetization exchange rate between water and macromolecules, which is directly affected by the level of protein composition in the tissue. Therefore, MTR represents the level of protein composition in tissues and is calculated as:

$$MTR = \left(\frac{M_0 - M_{MT}}{M_0}\right) \quad (1)$$
$$= 1 - \frac{M_{MT}}{M_0}$$

where MTR is the magnetization transfer ratio that indicates the level of protein composition, $M_{MT}$ and $M_0$ are the magnitude of water signals with and without the application of a MT pulse, respectively.

For tissues under HIFU treatment, focused ultrasound energy induces heat in tissues, which causes protein denaturation and thus a change in the protein composition. With MTR being a quantitative estimate on the level of protein composition, thermal ablation effects can be evaluated by monitoring the change in MTR (i.e., ΔMTR) during and after the course of treatment. For example, as shown in FIG. 3C, a gray-scale mapping of ΔMTR values over a region of tissue under thermal treatment indicates different degrees of protein denaturation in this region since the start of the treatment (here, higher gray bar values corresponding to more prominent thermal effects).

4 Proton Resonance Frequency Shift

Proton resonance frequency (PRF) shift technique is a non-invasive application of MRI. This technique can be used to measure a temperature distribution within an imaging area, as described by Ishihara et al., in *A Precise and Fast Temperature Mapping Using Water Proton Chemical Shift*, Magnetic Resonance in Medicine, Volume 34, Issue 6, Pages 814-823, the contents of which are incorporated herein by reference. Generally, changes in temperature induce rupture, stretching, or bending of hydrogen bonds, which causes a shift in the PRF. As this PRF shift is reflected in the phase of MR signals, temperature change can be determined by obtaining the phase information. For example, in some implementations where the MRI system uses a gradient echo sequence with an excitation RF pulse, temperature change can be obtained from:

$$\Delta T = \frac{\Delta\phi}{\alpha \cdot \omega_0 \cdot 2\pi \cdot TE} \quad (2)$$

where ΔT is the temperature change in Celsius, Δϕ is phase change in radians, α is thermal coefficient (~0.01 ppm/° C.), $\omega_0$ is Larmor frequency, and TE is the echo time used in gradient echo sequence.

5 Example of MR Pulse Sequence

In some examples in which the PRF shift and the MTR techniques are used to measure temperature and the degree of protein denaturation, respectively, in real-time, a MRI system uses pulse sequences that are suitable for generating MR signals that provide sufficient information for obtaining these two measurements. One example of such pulse sequences is described below.

Figure 4:
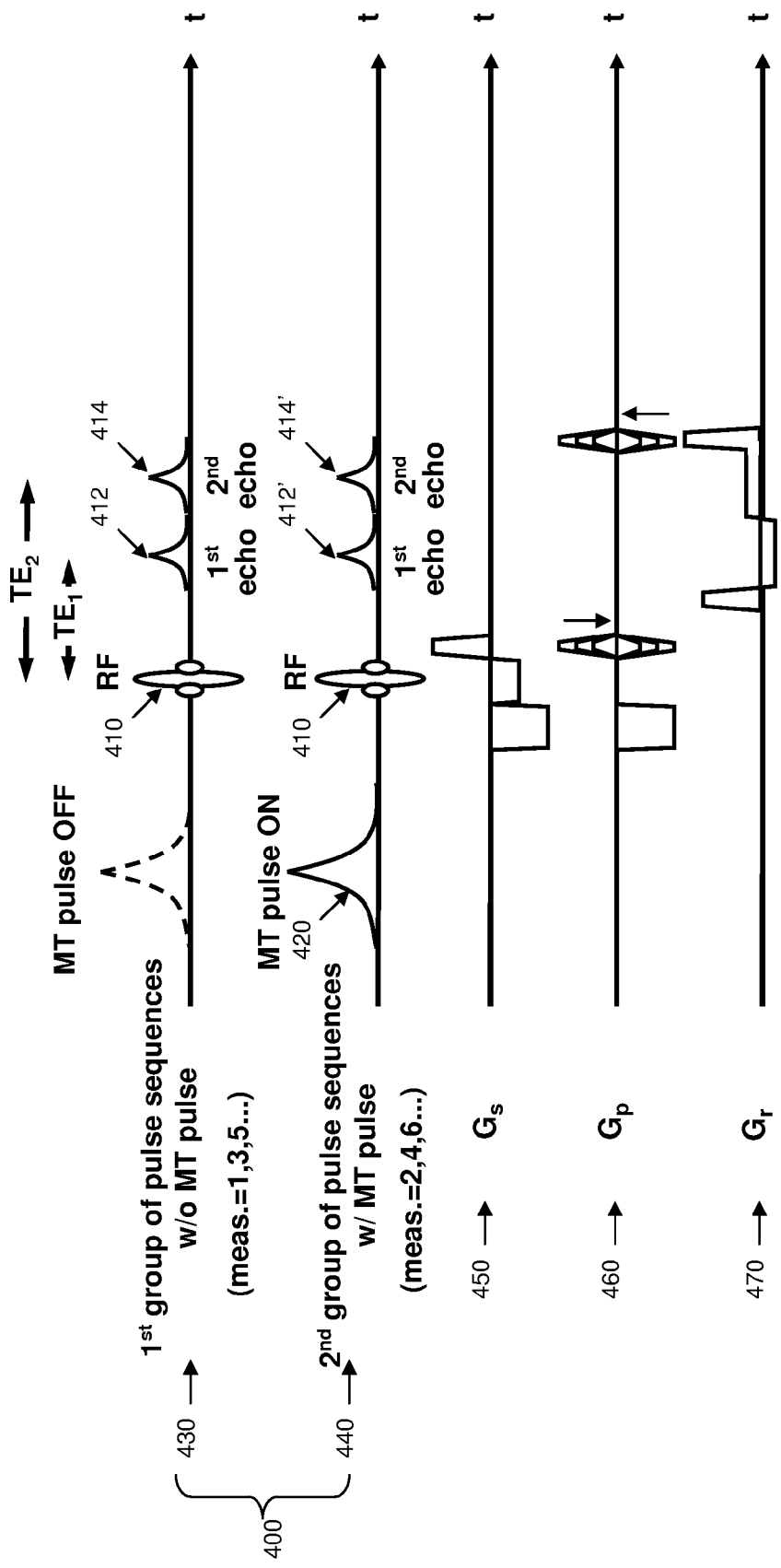
FIG. 4 is a diagram illustrating an exemplary magnetic resonance pulse sequence suitable for use in the MRI-guided HIFU system shown in FIG. 1.

Referring to FIG. 4, an exemplary implementation of MR pulse sequence 400 uses a dual gradient-echo design. Dual gradient echo pulse sequences are well known in the art and have been described e.g., by Kuperman V Y et. al., in *Differentiating Between T1 and T2*Changes Caused by Gadopentetate Dimeglumine in the Kidney by Using a Double-echo Dynamic MR Imaging Sequence*, Journal of Magnetic Resonance in Medicine, 1996 September-October; 6(5):764-8, the contents of which are incorporated herein by reference. The MR pulse sequence 400 includes a first group of MR pulse sequences 430 and a second group of MR pulse sequences 440, delivered to a tissue in alternating turns. Response signals to these pulse sequences are detected and processed in the following way to determine temperature and the degree of protein denaturation in real-time.

In the first group of MR pulse sequences 430, for example, a single RF pulse 410 excites a thin slice in a tissue and induces a first and second echo signal 412 and 414 at time $TE_1$ and $TE_2$, respectively. This slice of excitation is selected by a slice gradient 450 ($G_s$). Echo signals 412 and 414 in response to the excitation are detected by applying readout gradient 470 ($G_r$) during echo periods. Between the application of the RF pulse 410 and the readout gradient $G_r$, a phase-encoding gradient 460 ($G_p$) is applied orthogonally to $G_s$ and $G_r$. This phase-encoding gradient $G_p$ serves to encode and store relative phase information associated with each pixel in that direction throughout the slice. For instance, to construct a 128×128 pixels image, the RF pulse 410 is repeated 128 times with the field strength of $G_p$ changing in a stepwise fashion (e.g., with one subset of $G_p$ decreasing from maximum amplitude to zero and then increasing in the opposite direction until it reaches the maximum amplitude again). At the end of this pulse sequence, 128 lines (one for each phase encoding step) are produced, from which the phase information of each pixel in the slice can be extracted using a Fourier transformation.

Temperature information of the tissue is obtained from the phase information in the first echo signal 412 and/or the second echo signal 414. For example, based on equation (2), the change in tissue temperature from a baseline condition (e.g., before thermal treatment) is calculated, either using the change of phase in the first echo 412, as in $$\Delta T = \frac{\Delta \phi_1}{\alpha \cdot \omega_0 \cdot 2\pi \cdot TE_1} \quad (3)$$

or, using the change of phase in the second echo 414, as in $$\Delta T = \frac{\Delta \phi_2}{\alpha \cdot \omega_0 \cdot 2\pi \cdot TE_2} \quad (4)$$

where $\Delta\phi_1$ and $\Delta\phi_2$ are the change of phase from the baseline condition in the first and second echo signals, respectively. In some implementations, preferably, the second echo signal 414 (also referred to as the echo with long TE) is used for temperature calculation, since it has longer evolution time for phase accumulation, thereby providing a higher signal to noise ratio (SNR) compared with the first echo signal 412 (also referred to as the echo with short TE).

In the second group of MR pulse sequences 440, for example, a MT pulse 420 is applied before the RF pulse 410 and results in a new set of first and second echo signals 412' and 414'. These new echo signals 412' and 414' occur at the same echo time $TE_1$ and $TE_2$, but have different intensity from echo signals 412 and 414 that are generated by the RF pulse alone. As described earlier, the distinction between the two sets of echo signals can be used to calculate, based on equation (1), the magnetization transfer ratio MTR, which indicates the level of protein composition in the tissue.

For example, MTR can be calculated using a pair of first echo signals 412 and 412' generated with and without the MT pulse 420, by $$MTR = \left(\frac{M_0^{(1)} - M_{MT}^{(1)}}{M_0^{(1)}}\right) \quad (5)$$
$$= 1 - \frac{M_{MT}^{(1)}}{M_0^{(1)}}$$

where $M_0^{(1)}$ and $M_{MT}^{(1)}$ are the magnitude of echo signals 412 and 412', respectively. Similarly, MTR can be calculated using a pair of second echo signals 414 and 414', by $$MTR = \left(\frac{M_0^{(2)} - M_{MT}^{(2)}}{M_0^{(2)}}\right) \quad (6)$$
$$= 1 - \frac{M_{MT}^{(2)}}{M_0^{(2)}}$$

where $M_0^{(2)}$ and $M_{MT}^{(2)}$ are the magnitude of echo signals 414 and 414', respectively. In some implementations, preferably, MTR are determined primarily based on the first echo signals 412 and 412', since MT pulse-induced magnetization transfer effect generally decays over time.

Note that, unlike the calculation of MTR, which requires using a pair of echo signals generated under different levels of off-resonance magnetization saturation (e.g., with and without MT pulse), temperature measurement can be obtained from one echo signal alone. That is, each one of echo signals 412, 414, 412', 414' provides sufficient phase information for determining the temperature T of the tissue. In some examples, T is determined solely from the second echo signal 414 or signal 414'. In some examples, to improve accuracy, T is determined by combining (e.g., averaging) the temperature measurements obtained from signals 414 and 414'. In some other examples, T is determined by using the phase information in both the first group of echo signals (412 and 414) and the second group of echo signals (412' and 414').

The MR pulse sequence suitable for the application described above may be designed and modified in various ways. For example, instead of using a dual gradient-echo sequence, it is possible to adopt other pulse sequences to induce response signals that provide temperature information. MT pulses of various frequencies and amplitude may be interleaved (e.g., alternated) between the deliveries of these pulse sequences to generate response signals representing different levels of off-resonance magnetization saturation, based on which the MTR can be obtained to provide an estimate on the degree of protein denaturation during thermal procedures. In some examples in which MR pulse sequences include dual gradient echo sequences, both the temperature and protein composition measurements can be obtained based on the first echo signals, the second echo signals, or a combination thereof.

6 Experimental Results 6.1 Experiment One

This experiment shows the accuracy and feasibility of detecting temperature change and MTR on a pre-heated phantom.

Figure 5B:
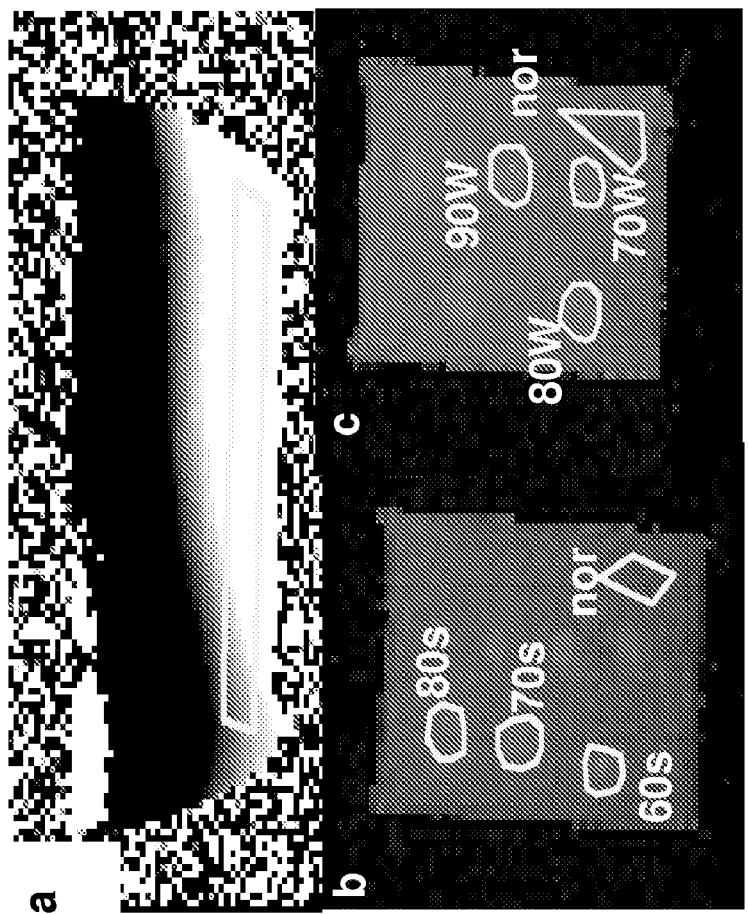
FIGS. 5A-5C illustrate the experimental results of Experiment 1.
Figure 5A:
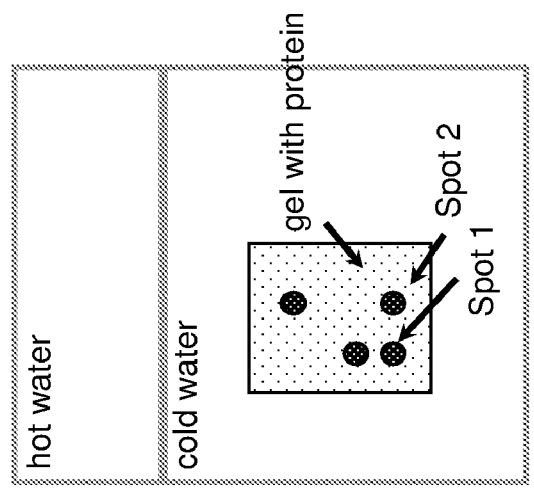

FIG. 5A depicts a sample prepared for this experiment. This sample included a first part containing hot water used for monitoring temperature change during scanning, and a second part containing a gel phantom immersed in cold water. The gel phantom had multiple spots (including spot 1 and spot 2) pre-treated with HIFU heating for observing the change of MTR over time. Table 1 below shows the HIFU power and heating time used for treating these spots.

TABLE 1

| Phantom 1 | | | Phantom 2 | | |
|---|---|---|---|---|---|
| power (W) | Time (sec) | MTR contrast (a.u.) | power (W) | time (sec) | MTR contrast (a.u.) |
| 60 | 60 | 0.0397 | 70 | 30 | 0.0318 |
| 60 | 70 | 0.0710 | 80 | 30 | 0.0573 |
| 60 | 80 | 0.0809 | 90 | 30 | 0.0874 |

As shown in the table, two sets of MT phantom were applied. Phantom 1 used fixed HIFU power (60 W) with varying heating period, whereas phantom 2 used varying HIFU power with a constant heating period (30 s).

MR images were acquired on a 3 Tesla clinical MRI system. MR pulse sequences adopted a dual gradient-echo design, with ON and OFF of the MT pulse interleaved. Imaging parameters included: TR (repetition time)=42 ms, TE (short/long echo time)=4.52/20 ms, flip angle=15°, FOV (field of view)=160×160 mm$^2$, matrix size=128 pixels×128 pixels, slice thickness=1.5 mm, off-resonance frequency of MT pulse (compared with on-resonance frequency of RF pulse)=+500 Hz. As control, the temperature in hot water was continuously measured by a thermometer placed near the bottom of the sample.

Figure 5C:
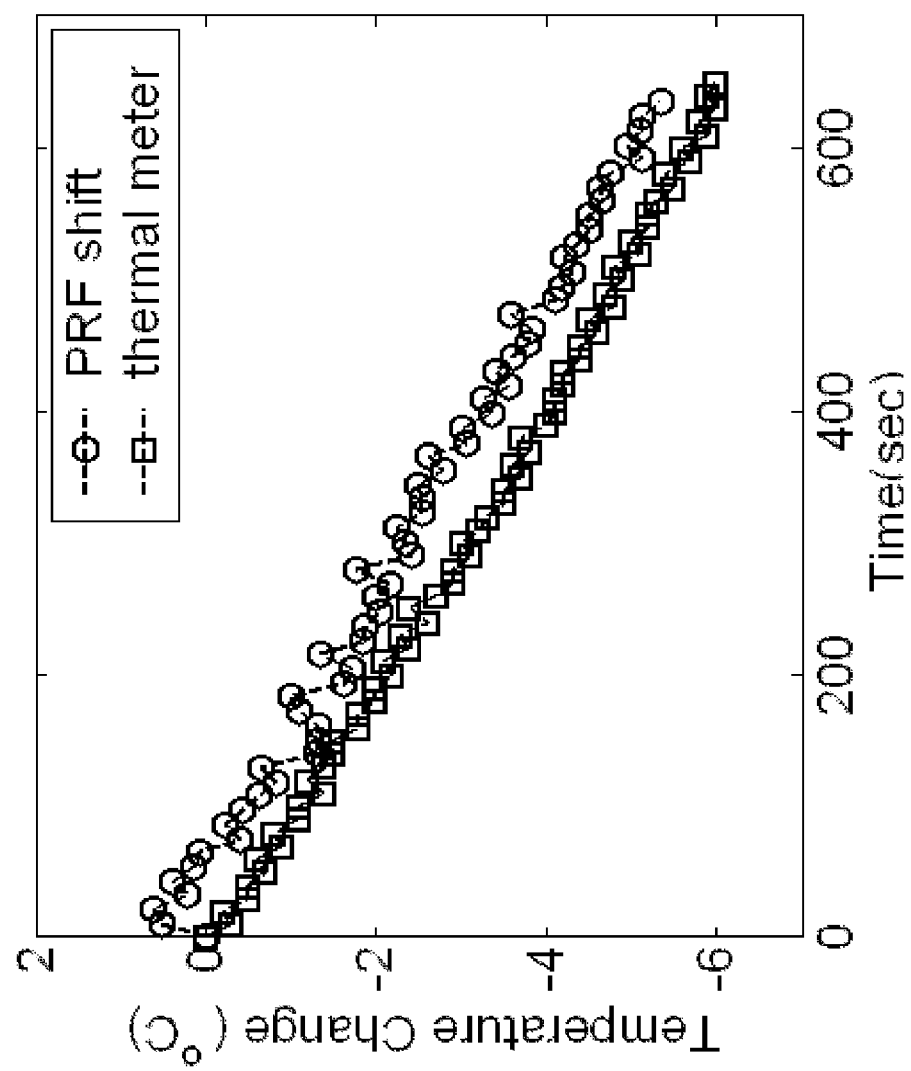

FIG. 5B shows several regions of interest (ROIs) selected from MTR images for comparing the difference of MTR values between HIFU-heated spots and areas without HIFU heating. FIG. 5C shows the temperature changes in the bottom of hot water measured by using the PRF shift technique and thermometer, respectively. The consistent results achieved by these two methods indicated that PRF shift technique can be used for continuous temperature monitoring with high accuracy.

Also shown in Table 1 are measured MTR contrast values of HIFU-heated spots. In Phantom 1, under fixed HIFU power, MTR contrast values increased from 0.0397 to 0.0809 with increasing HIFU heating duration; while in phantom 2, with fixed heating duration, MTR contrast values increased from 0.0318 to 0.0874 with increasing HIFU power. These measurements are in good agreement with theoretical predictions.

6.2 Experiment Two

This experiment goes further to show the accuracy and feasibility of monitoring temperature change and MTR in an ex vivo porcine liver tissue.

Pulsed-wave HIFU pulses with power of 83 Watt were performed on a porcine liver tissue immersed in 25° C. degassed water. Serial MR images were acquired during pre-heating (t=0~19 sec), heating (t=20~122 sec) and post-heating (t=123~223 sec) periods. All MR images were acquired on a 3Tesla clinical MRI system. MR pulse sequences adopted a dual gradient-echo design, with ON and OFF of the MT pulse interleaved. Imaging parameters included: TR=29 ms, TE=3.61/7.57 ms, flip angle=20°, FOV=160×120 mm$^2$, matrix size=128 pixels×85 pixels, slice thickness=3 mm, off-resonance frequency of MT pulse=−450 Hz. Temporal resolution of about 1.85 sec for monitoring temperature change and observing MTR change was achieved simultaneously. To evaluate the consistency of MTR measurements, the same pulse sequence was performed for 32 seconds starting at 2 minutes after turning off the HIFU heating pulses. The changes of temperature and MTR were plotted with respect to heating time, using several ROIs selected in both the heated and non-heated areas (2 cm away from the heated area) from the phase and magnitude (with MT pulses) images.

Figure 6B:
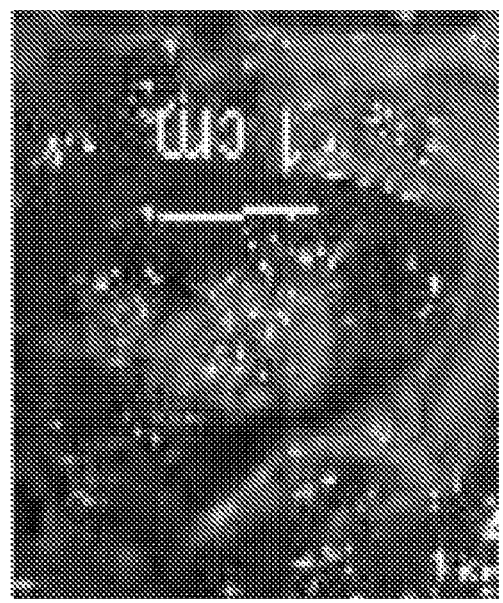
FIGS. 6A-6E illustrate the experimental results of Experiment 2.
Figure 6A:
Figure 6A:
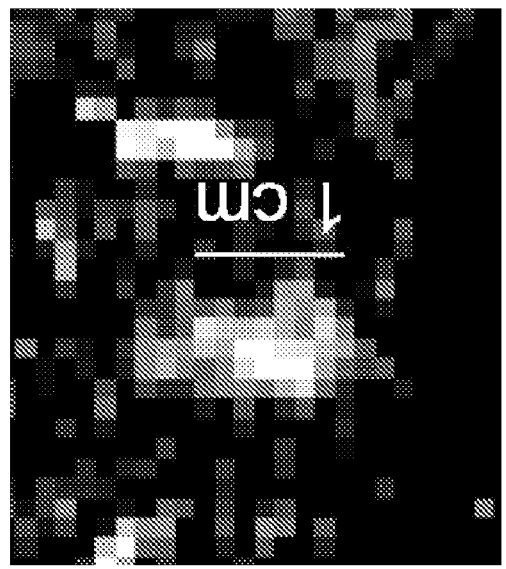
Figure 6D:
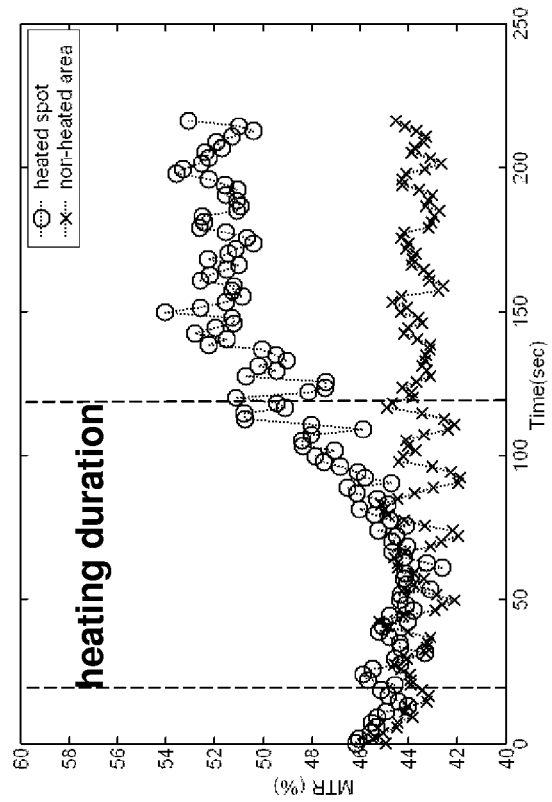
Figure 6C:
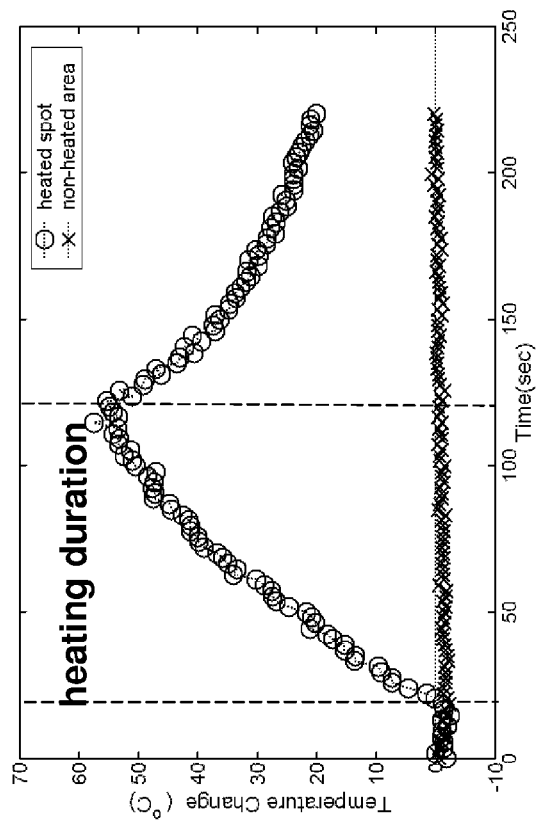
Figure 6E:
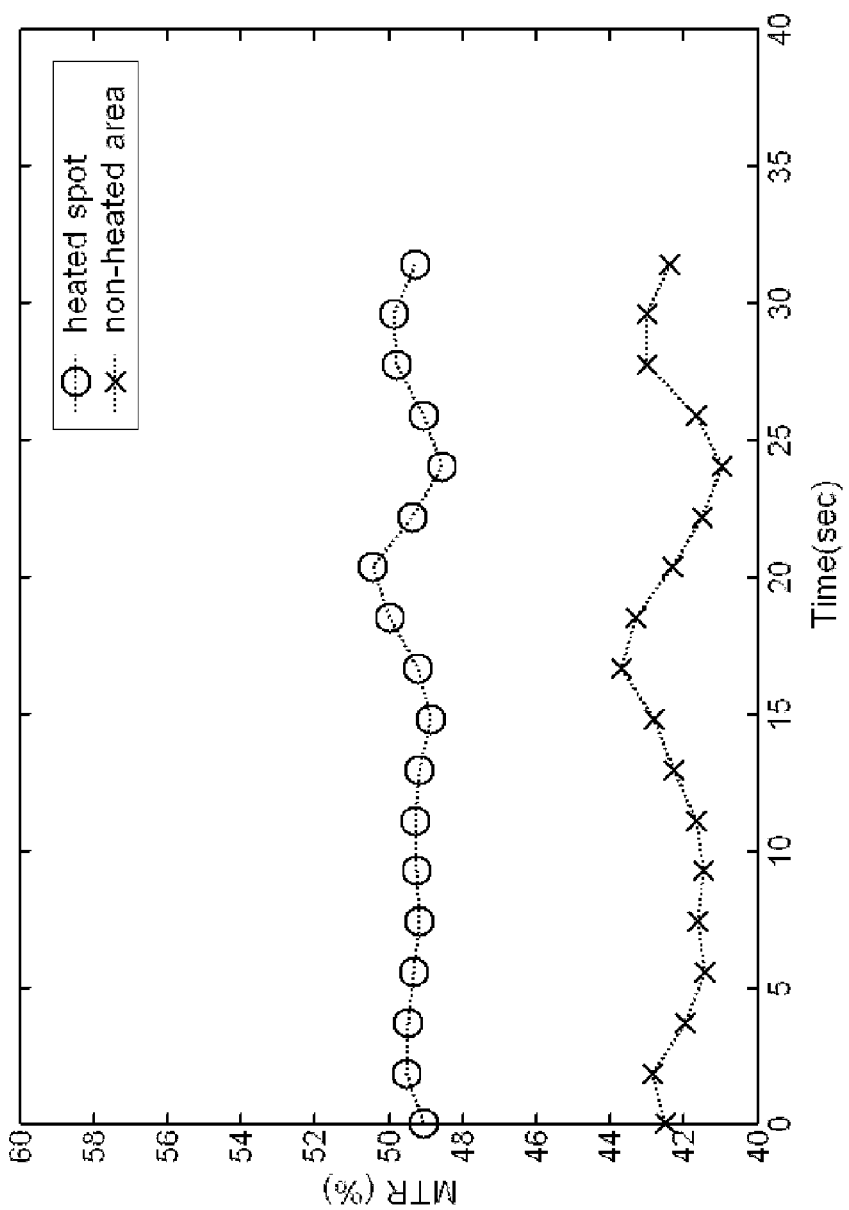

FIG. 6A shows a MTR map of the heated tissue obtained two minutes after heating, and FIG. 6B shows an optical image of the cut face of the same tissue. Both images contain the same region of burned lesion (about 1 cm in diameter). FIG. 6C shows the temperature changes in the heated and non-heated areas with respect to time. The temperature change in the heated areas reached a peak of about 60° C., whereas the temperature in the non-heated areas remained 0° C. during the course of the experiment. FIG. 6D shows the change of MTR in the heated and non-heated areas. While MTR in non-heated area remained at 43.5%, in the heated areas, it increased gradually from 45% to 52% (at about t=150 s) and afterwards maintained at this level. This increase in MTR by 16% from the original level was distinguishable from that in the non-heated areas. FIG. 6E further shows that such elevation of MTR remained for 2 minutes after the HIFU heating pulses were turned off.

Note that software instructions to each of the MRI guided HIFU Controller 190, the MRI controller 132, and the HIFU Controller 182 may be tangibly embodied in an information carrier, e.g., in a machine-readable storage device or in a propagated signal, for execution by, or to control the operation of, data processing apparatus, e.g., a programmable processor, a computer, or multiple computers. The instructions can be written in any form of programming language, including compiled or interpreted languages, and it can be deployed in any form, including as a stand-alone program or as a module, component, subroutine, or other unit suitable for use in a computing environment. The instructions can be deployed to be executed on one computer or on multiple computers at one site or distributed across multiple sites and interconnected by a communication network.

Processors suitable for the execution of these instructions include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Information carriers suitable for embodying these instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

It is to be understood that the foregoing description is intended to illustrate and not to limit the scope of the invention, which is defined by the scope of the appended claims. Other embodiments are within the scope of the following claims.

What is claimed is:

1. A method for detecting temperature and protein denaturation of a tissue, said method comprising:
    generating a plurality of MR pulse sequences, including a first group of pulse sequences lacking MT pulses and a second group of pulse sequences having MT pulses, wherein the first and second groups of pulse sequences are interleaved;
    delivering the plurality of MR pulse sequences to the tissue;
    receiving a plurality of response signals, including a first group of response signals in response to the first group of pulse sequences, and a second group of response signals in response to the second group of pulse sequences;
    determining a first information associated with a degree of protein denaturation of the tissue based on the first and second groups of response signals to thereby detect protein denaturation of the tissue; and
    determining a second information associated with a change in temperature of the tissue based on at least some of the plurality of response signals to thereby detect temperature of the tissue,
    wherein the first information and the second information are determined simultaneously.

2. The method of claim 1, wherein the plurality of MR pulse sequences are configured to be suitable for inducing response signals that are sufficient for determining the first and second information.

3. The method of claim 1, wherein the plurality of MR pulse sequences include dual gradient echo sequences.

4. The method of claim 3, wherein each one of the plurality of response signals includes a first echo component and a second echo component.

5. The method of claim 4, wherein said determining the first information includes comparing at least some of the first echo components of the first group of response signals with some of the first echo components of the second group of response signals.

6. The method of claim 4, wherein said determining the second information includes comparing at least some of the second echo components of the first group of response signals with some of the second echo components of the second group of response signals.

7. The method of claim 1, wherein each one of the first group of pulse sequences includes a RF excitation pulse, and each one of the second group of pulse sequences includes the RF excitation pulse and a MT pulse.

8. The method of claim 7, wherein the MT pulse includes an off-resonance pulse.

9. The method of claim 7, wherein the MT pulse is configured to cause a change in the response signals induced by the RF excitation pulse alone.

10. The method of claim 1, wherein said determining the first information includes comparing the first group of response signals with the second group of response signals.

11. The method of claim 1, wherein the first information includes a magnetization transfer ratio, and the second information includes a phase information.

12. The method of claim 1, further comprising reconstructing an image and forming a temperature map of the tissue based on the plurality of response signals.

13. A method of MRI-guided thermal therapy on a tissue, comprising:
generating a plurality of MR pulse sequences, including a first group of pulse sequences lacking MT pulses and a second group of pulse sequences having MT pulses, wherein the first and second groups of pulse sequences are interleaved;
delivering the plurality of MR pulse sequences to the tissue;
receiving, for each of the plurality of MR pulse sequences, a response signal,
determining a first information associated with a degree of protein denaturation of the tissue based on the first and second groups of response signals to thereby detect protein denaturation of the tissue;
determining a second information associated with a change in temperature of the tissue based on at least some of the plurality of the response signals to thereby detect temperature of the tissue;
accepting specifications of a treatment plan having a plurality of sessions, each associated with one of a plurality of regions of the tissue; and
controlling each of the plurality of sessions based on the first and second information,
wherein the first information and the second information are determined simultaneously.

14. The method of claim 13, wherein controlling each of the plurality of sessions includes initiating and terminating said session.

15. The method of claim 14, wherein the treatment plan further includes a criterion for initiating and terminating each of the plurality of sessions.

16. The method of claim 15 wherein the criterion is associated with the change in temperature of the tissue.

17. The method of claim 15 wherein the criterion is associated with the degree of protein denaturation of the tissue.

18. The method of claim 13, wherein each one of the first group of pulse sequences includes a RF excitation pulse, and each one of the second group of pulse sequences includes the RF excitation pulse and a MT pulse.

19. A system for detecting temperature and protein denaturation of a tissue, said system comprising a controller configured for:
generating a plurality of pulse sequences, including a first group of pulse sequences lacking MT pulses, and a second group of pulse sequences having MT pulses, wherein the first and second groups of pulse sequences are interleaved;
receiving a plurality of response signals, including a first group of response signals in response to the first group of pulse sequences, and a second group of response signals in response to the second group of pulse sequences;
determining simultaneously a first information associated with a degree of protein denaturation of the tissue based on the first and second groups of response signals and a second information associated with a change in temperature of the tissue based on at least some of the plurality of response signals, thereby detecting protein denaturation and temperature of tissue.

20. The system of claim 19, further comprising a subsystem configured for delivering the plurality of pulse sequences and detecting the plurality of response signals.

21. The system of claim 20, wherein the subsystem includes a MRI system and the plurality of pulse sequences include MR pulse sequences.

22. The system of claim 19, wherein the plurality of pulse sequences are configured to be suitable for inducing response signals that are sufficient for determining the first and second information.

23. The system of claim 19, wherein the plurality of pulse sequences includes dual-gradient echo sequences.

24. The system of claim 19, wherein each one of the first group of pulse sequences includes a RF excitation pulse, and each one of the second group of pulse sequences includes the RF excitation pulse and a MT pulse.

25. The system of claim 24, wherein each one of the plurality of response signals includes a first echo component and a second echo component, and the controller determines the first information based on at least some of the first echo components of the first group of response signals and at least some of the first echo components of the second group of response signals.

26. The system of claim 19, wherein the controller is further configured for reconstructing an image and forming a temperature map of the tissue based on the plurality of response signals.

* * * * *